(12) United States Patent
Svatos et al.

(10) Patent No.: US 6,822,252 B2
(45) Date of Patent: Nov. 23, 2004

(54) VERIFICATION OF ELECTRON TREATMENT FIELDS

(75) Inventors: Michelle Marie Svatos, Oakland, CA (US); William F. Collins, Clayton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 205 days.

(21) Appl. No.: 09/910,526

(22) Filed: Jul. 20, 2001

(65) Prior Publication Data

US 2003/0201403 A1 Oct. 30, 2003

(51) Int. Cl.[7] .................................................. H01J 3/00
(52) U.S. Cl. .................................... 250/505.1; 378/65
(58) Field of Search ........................ 250/505.1; 378/65, 378/147, 146, 151, 152

(56) References Cited

U.S. PATENT DOCUMENTS

| | | | |
|---|---|---|---|
| 4,220,866 A | | 9/1980 | Taumann et al. |
| 4,726,046 A | * | 2/1988 | Nunan ........................ 378/65 |
| 4,880,985 A | | 11/1989 | Jones |
| 5,160,847 A | * | 11/1992 | Leavitt et al. ........... 250/505.1 |
| 5,396,889 A | * | 3/1995 | Ueda et al. ................. 600/407 |
| 5,813,985 A | * | 9/1998 | Carroll ....................... 600/436 |
| 6,167,114 A | | 12/2000 | Siochi |
| 6,222,544 B1 | | 4/2001 | Tarr et al. |
| 6,429,578 B1 | * | 8/2002 | Danielsson et al. ... 313/105 CM |
| 6,449,335 B1 | | 9/2002 | Siochi |
| 6,477,229 B1 | | 11/2002 | Grosser |

FOREIGN PATENT DOCUMENTS

| | | |
|---|---|---|
| JP | 7116276 A | 5/1995 |
| JP | 11216196 A | 8/1999 |
| JP | 2001276238 A | 10/2001 |
| WO | WO 00/13189 | 3/2000 |

OTHER PUBLICATIONS

Ma et al., "Energy–and intensity–modulated electron beams for radiotherapy" (IOP Publishing Ltd, vol. 45, No. 8, Aug. 1, 2000; pp. 2293–2311).

Karlsson et al. "Treatment head design for multileaf coellimated high–energy electrons" (Medical Physics, vol. 26, No. 10, Oct. 1999, pp. 2161–2167).

Moran et al. "Characteristics of scattered electron beams shaped with a multileaf collimator", (Medical Physics, vol. 24, No. 9, Sep. 1997; pp. 1491–1498).

Zhu et al. "Characteristics of bremsstrahlung in electron beams"(Medical Physics, vol. 28, No. 7, Jul. 2001; pp. 1352–1358).

* cited by examiner

Primary Examiner—Kiet T. Nguyen (57) ABSTRACT

A system, method, apparatus, and means for verifying an electron treatment field include positioning an image detector, and operating the image detector to detect an image created by photons generated in the delivery of an electron treatment beam. The image is manipulated to generate a representation of the electron treatment field.

27 Claims, 7 Drawing Sheets

VERIFICATION OF ELECTRON TREATMENT FIELDS

CROSS-REFERENCE TO RELATED APPLICATIONS

This application is related to commonly owned U.S. patent application Ser. No. 09/909,589, filed Jul. 20, 2001 (on even date herewith), Attorney Docket No. 2001P13116US for "AUTOMATED DELIVERY OF TREATMENT FIELDS", and U.S. patent application Ser. No. 09/909,513, filed Jul. 20, 2001 (on even date herewith), Attorney Docket No. 2001P13112US for "REMOVABLE ELECTRON MULTILEAF COLLIMATOR", the contents of each of which are incorporated by reference in their entirety for all purposes.

BACKGROUND OF THE INVENTION

1. Field of the Invention

The present invention relates generally to radiation therapy devices, and more particularly, to the verification of treatment fields of radiation therapy devices.

2. Description of the Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

Both primary photon and primary electron beams may be used in radiation therapy. Accordingly, many existing radiation therapy devices include the ability to generate and deliver both photon and electron beams. Currently, clinical practice requires substantial manual intervention to use conformal electron treatment. Conformal photon fields typically are shaped using one or more collimating devices positioned between the source and the treatment area. Many of these photon beam collimating devices may be positioned automatically to deliver a desired photon field shape to a treatment area on a patient. Little manual intervention is required to administer photon radiation therapy.

Primary electrons are currently used on approximately 30% of all patients who undergo radiation therapy. Electron fields delivered via radiation therapy devices are typically shaped using either an off-the-shelf electron applicator (either rectangular or circular in cross-section) or a custom cutout formed of Cerrobend®. Both of these beam shaping methods have limitations. Off-the-shelf electron applicators often unnecessarily irradiate portions of healthy tissue, since they do not precisely conform to the target. Custom cutouts formed of Cerrobend® are highly conformal, but are costly to make, store and require special quality assurance. The Cerrobend® material may also require special handling because of the potentially toxic metals involved. Each of these approaches to electron field shaping also suffer in that they can be inefficient to use. A radiation therapist delivering a prescribed treatment must repeatedly enter the treatment room during treatment to insert the proper cutout for each field in the therapy. This is not only inefficient, but it effectively precludes the delivery of treatments which require electron field modulation in both intensity and energy at a single gantry position.

As described in co-pending and commonly assigned U.S. patent application Ser. Nos. 09/909,589, and 09/909,513 (referenced above), Applicants have developed a radiation therapy device and electron collimator which overcome many of these difficulties associated with delivery of both electron and photon beams from a single radiation therapy device.

Many radiation therapy devices utilize portal imaging techniques to verify and record the patient tumor location. Portal images are images of the patient portal through which the therapeutic radiation passes. These images can be taken before or after treatment to ascertain that the patient position, as well as the beam shape, conform to a desired treatment plan. Photon radiation therapy is well-suited to portal imaging because photons freely pass through the patient's body, allowing an image to be taken after the photons pass through the body.

Electron therapies, on the other hand, heretofore have not been suited to portal imaging, because electrons are not transmitted completely through the patient's body. This characteristic of electron treatments is desirable in that it ensures that almost no dose is delivered to sensitive body structures downstream from the treatment zone; however, it makes it difficult to determine whether the beam shape and patient position are correct. Accordingly, before undertaking an electron treatment, radiation therapists typically irradiate the patient with a dose of photon radiation to capture a conventional portal image. However, this solution suffers from a number of disadvantages, including the irradiation of sensitive areas of the patient to a dose of photon radiation (which electron radiation therapy is intended to avoid), and because it is not a true record of the actual treatment which will be delivered via a potentially-differently shaped electron field, further, the patient may move during the time between delivery of the photon dose and the subsequent electron therapy.

It would be desirable to provide a system and method for electron portal imaging which overcomes the drawbacks of previous systems. It would further be desirable to provide a system and method which allows efficient, accurate, and effective verification of electron treatment fields. It would further be desirable to provide effective verification of mixed beam treatments involving the application of both primary electrons and primary photons in a single course of treatment.

SUMMARY OF THE INVENTION

To alleviate the problems inherent in the prior art, and to allow the accurate, efficient and effective delivery of photon, electron, and mixed beam radiation therapy, embodiments of the present invention provide a system and method for the verification of electron treatment fields.

According to one embodiment of the present invention, a system, method, apparatus, and means for verifying an electron treatment field include positioning an image detector, and operating said image detector to detect an image created by photons generated in the delivery of an electron treatment beam. In some embodiments, the image is manipulated to generate a representation of the electron treatment field. In some embodiments, the image detector is a flat panel imaging device, such as a device using solid state sensors. In some embodiments, amorphous silicon solid state sensors are used. In some embodiments, the image detector comprises video technology to capture an image created by photons generated in the delivery of the electron treatment beam.

According to some embodiments, the image is manipulated by determining an energy of the electron treatment beam, calculating an angular dependence of the photons on the electron treatment beam, and generating the representation of the electron treatment field based on the detected image and the angular dependence.

According to some embodiments, the image is manipulated by comparing the image to an open field image to generate an enhanced image of the electron treatment field. According to one embodiment, the detection device may be used to verify fields for primary photon and primary electron therapies as well as mixed beam therapies.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION

The following description is provided to enable any person skilled in the art to make and use the invention and sets forth the best modes contemplated by the inventor for carrying out the invention. Various modifications, however, will remain readily apparent to those skilled in the art.

Figure 1:
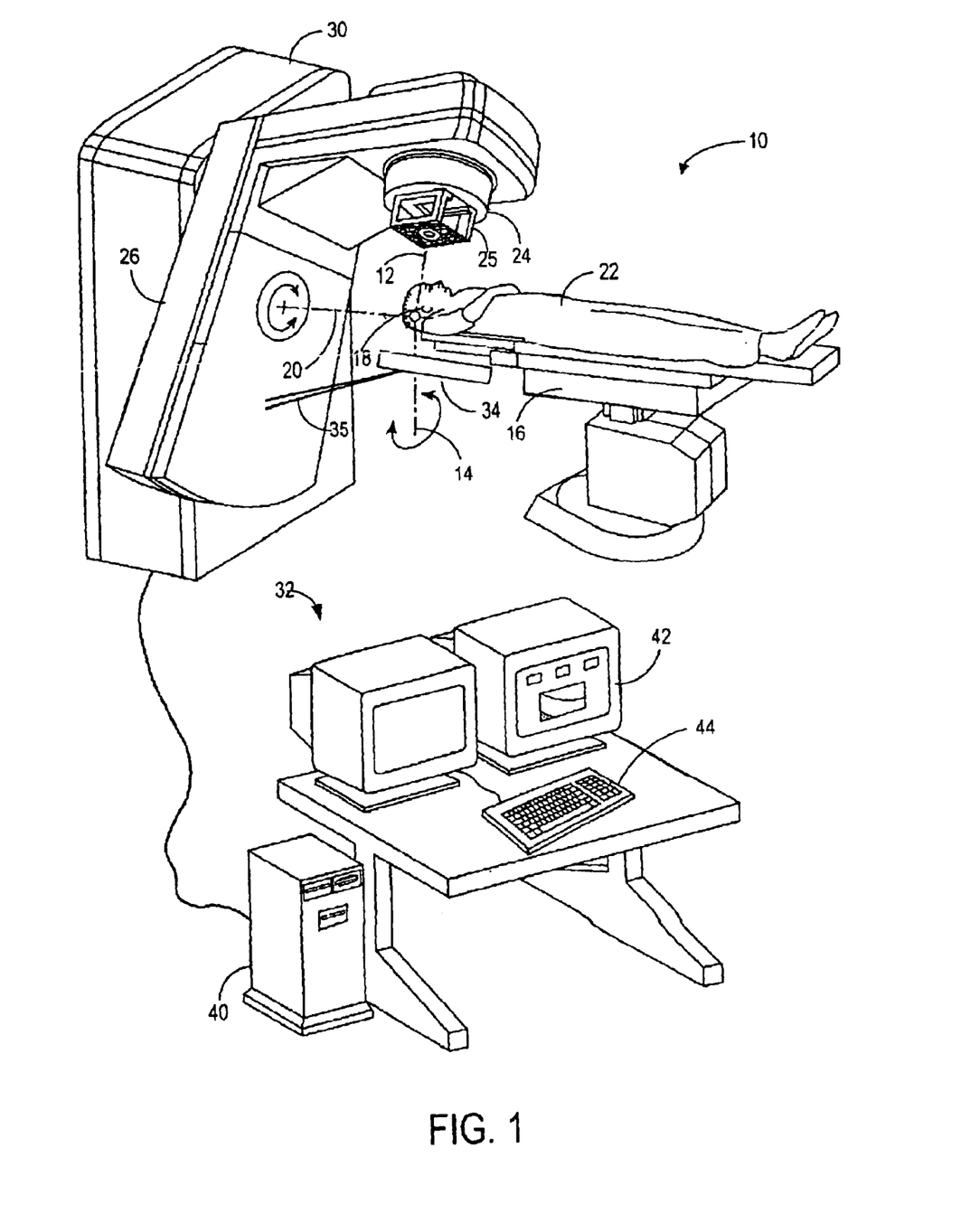
FIG. 1 is diagram illustrating a radiation therapy device.

Turning now to the drawings and, with particular attention to FIG. 1, a radiation therapy device 10 pursuant to embodiments of the present invention is shown. According to one embodiment of the present invention, radiation therapy device 10 includes a beam shielding device (not shown) within a treatment head 24, a control unit in a housing 30 and a treatment unit 32. An accessory tray 25 is mounted to an exterior of treatment head 24. Accessory tray 25, in one embodiment, is configured to receive and securely hold attachments used during the course of treatment planning and treatment (such as, for example, reticles, wedges, or the like).

Radiation therapy device 10 includes a gantry 26 which can be swiveled around a horizontal axis of rotation 20 in the course of a therapeutic treatment. Treatment head 24 is fastened to a projection of the gantry 26. A linear accelerator (not shown) is located inside gantry 26 to generate the high energy radiation required for the therapy. The axis of the radiation bundle emitted from the linear accelerator and the gantry 26 is designated by beam path 12. Electron, photon or any other detectable radiation can be used for the therapy. Embodiments of the present invention permit the controlled delivery of both primary electron and primary photon beams to a treatment zone 18 during the course of a prescribed treatment.

During a course of treatment, the radiation beam is trained on treatment zone 18 of an object 22, for example, a patient who is to be treated and whose tumor lies at the isocenter of the gantry rotation. The plates or leaves of the beam shielding device within the treatment head 24 are substantially impervious to the emitted radiation. The collimator leaves or plates are mounted between the radiation source and the patient in order to delimit (conform) the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

According to one embodiment of the present invention, several beam shaping devices are used to shape radiation beams directed toward treatment zone 18. In one embodiment, a photon collimator and an electron collimator are provided. Each of these collimators, as will be described further below, may be separately controlled and positioned to shape beams directed at treatment zone 18. According to one embodiment, the photon collimator (not shown in FIG. 1) is contained within treatment head 24 and the electron collimator (not shown in FIG. 1) is removably mounted on accessory tray 25.

According to one embodiment of the present invention, radiation therapy device 10 includes a detector 34 which is used, as will be described further below, to perform portal imaging for both photon treatments and electron treatments. Detector 34 may be attached to gantry 26 via an arm structure 35. In some embodiments, arm structure 35 may be remotely operated by an operator to position detector 34 in a desired position.

Detector 34, in one currently-preferred embodiment, is a flat panel imaging device using solid state amorphous silicon sensors. The RID 1640, offered by PerkinElmer®, Inc. of Fremont Calif., is one suitable device. In one embodiment, the imaging device used as detector 34 is formed with a plurality of detector elements formed in a two dimensional array. In one embodiment, each detector element (or "pixel") in the array is a solid state sensor, such as a solid state amorphous silicon sensor. Operation of detector 34 may result in the capture of a two dimensional image. In one embodiment, computer 40 and detector control 49 operate to control detector 34 to capture an image and map the signal detected by each of the detector elements to a gray scale value, providing a graphical depiction of the captured image. Preferably, the imaging device used as detector 34 has sufficient sensitivity and dynamic range to detect low signals or amounts of photons.

For example, in a radiation therapy which provides a therapeutic beam of electrons at 6 MeV, Applicants have been able to develop useful portal images where 50 Monitor Units of electrons are delivered to the treatment area, and where only 5% of the total electrons are converted into bremsstrahlung photons. Preferably, the imaging device used as detector 34 has sufficient dynamic range to detect such low amounts of photons as well as higher amounts of photons delivered in higher energy photon treatments (e.g., in a primary photon treatment at 21 MV, approximately 50 Monitor Units of photons per gantry angle may be delivered to the treatment zone and detected by detector 34).

According to one embodiment of the invention, detector 34 is used to verify electron treatment fields delivered by radiation therapy device 10 by detecting bremsstrahlung photons produced incidental to the generation of the electron treatment field. Applicants have discovered that sufficient bremsstrahlung photons are generated in radiation therapy device 10 to allow the capture of a portal image on detector 34. These bremsstrahlung photons are primarily generated in treatment head 24 as a result of scattering effects, however, Applicants believe that other scattering may be produced as the electron beam passes the photon and electron collimators along the beam path. Applicants believe that approximately 5% of the incident electron beam is converted to bremsstrahlung photons in treatment head 24 and that a few more bremsstrahlung photons are created as the electron beam passes the photon and electron collimators. The small percentage of the incident electron beam that is converted to bremsstrahlung photons can be captured using detector 34. The captured image is then corrected to create an image of the electron field, thereby allowing quick and efficient verification of the treatment field including patient anatomy, position and the field shape.

Detector 34 may be attached to gantry 26 via arm structure 35 or in some other manner which allows it to be removably placed under patient 22. In other embodiments, detector 34 may be permanently attached to table 16, or movably attached to table 16 such that it may be selectively moved into imaging position as desired. In some embodiments, detector 34 may be used only to verify electron treatment fields. In other embodiments, detector 34 is used to verify both electron and photon treatment fields.

Radiation therapy device 10 also includes a central treatment processing or control unit 32 which is typically located apart from radiation therapy device 10. Radiation therapy device 10 is normally located in a different room to protect the therapist from radiation. Treatment unit 32 includes a processor 40 in communication with an operator console 42 (including one or more visual display units or monitor) and an input device such as a keyboard 44. Data can be input also through data carriers such as data storage devices or a verification and recording or automatic setup system. More than one control unit 32, processor 40, and/or operator console 42 may be provided to control radiation therapy device 10.

Treatment processing unit 32 is typically operated by a therapist who administers actual delivery of radiation treatment as prescribed by an oncologist. Therapist operates treatment processing unit 32 by using keyboard 44 or other input device. The therapist enters data defining the radiation dose to be delivered to the patient, for example, according to the prescription of the oncologist. The program can also be input via another input device, such as a data storage device. Various data can be displayed before and during the treatment on the screen of operator console 42. According to one embodiment of the present invention, treatment processing unit 32 receives imaging information from detector 34, allowing the radiation therapist to make any necessary pre-treatment beam or positioning adjustments.

Embodiments of the present invention permit the delivery of both primary electron and primary photon beams to treatment zone 18 during the course of a prescribed treatment. Embodiments of the present invention permit the creation and control of both photon and electron radiation beams which closely match the shape and size of treatment zone 18. Further, embodiments of the present invention permit the verification of both electron and photon treatment fields.

Figure 2:
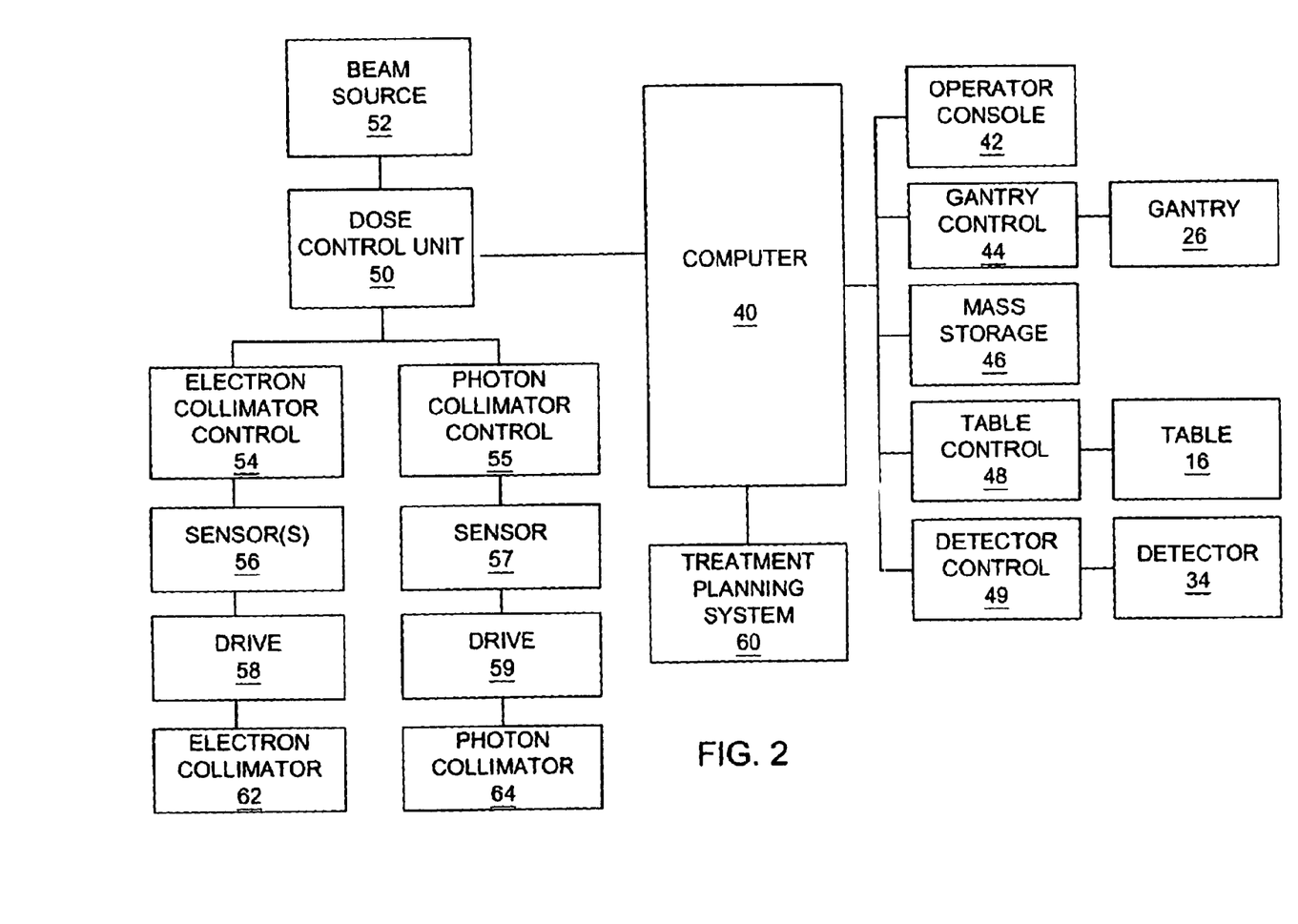
FIG. 2 is a block diagram illustrating portions of the radiation therapy device of FIG. 1 according to one embodiment of the present invention.

Referring now to FIG. 2, a block diagram is shown depicting portions of a radiation therapy device 10 and treatment unit 32 according to one embodiment of the present invention. In particular, treatment delivery elements of a radiation therapy device are shown, which may be configured in radiation therapy device 10 and treatment unit 32 as depicted in FIG. 1. The treatment delivery elements include a computer 40, operatively coupled to an operator console 42 for receiving operator control inputs and for displaying treatment data to an operator. Operator console 42 is typically operated by a radiation therapist who administers the delivery of a radiation treatment as prescribed by an oncologist. Using operator console 42, the radiation therapist enters data that defines the radiation to be delivered to a patient.

Mass storage device 46 stores data used and generated during the operation of the radiation therapy device including, for example, treatment data as defined by an oncologist for a particular patient. This treatment data is generated, for example, using a treatment planning system 60 which may include manual and computerized inputs to determine a beam shape prior to treatment of a patient. Treatment planning system 60 is typically used to define and simulate a beam shape required to deliver an appropriate therapeutic dose of radiation to treatment zone 18.

Data defining the beam shape and treatment are stored, e.g., in mass storage device 46 for use by computer 40 in delivering treatment. According to one embodiment of the present invention, treatment planning may include activities which occur prior to the delivery of the treatment, such as the generation of treatment data defining a photon treatment, an electron treatment, and/or a mixed beam treatment. Embodiments of the present invention permit the use of mixed beam treatments without the need for extended disruptions to install electron applicators or other shielding devices. Further, embodiments of the present invention permit field shaping of electron beams during a treatment in a device which also permits field shaping of photon beams during a treatment. Embodiments of the present invention also permit the verification of photon, electron, and mixed beams.

Although a single computer 40 is depicted in FIG. 2, those skilled in the art will appreciate that the functions described herein may be accomplished using one or more computing devices operating together or independently. Those skilled in the art will also appreciate that any suitable general purpose or specially programmed computer may be used to achieve the functionality described herein.

Computer 40 is also operatively coupled to various control units including, for example, a gantry control 44 and a table control 48. In operation, computer 40 directs the movement of gantry 26 via gantry control 44 and the movement of table 16 via table control 48. These devices are controlled by computer 40 to place a patient in a proper position to receive treatment from the radiation therapy device. In some embodiments, gantry 26 and/or table 16 may be repositioned during treatment to deliver a prescribed dose of radiation.

According to one embodiment of the present invention, computer 40 is operatively coupled to a detector control 49. Detector control 49 is used to control the operation of detector 34 to perform treatment field verifications pursuant to embodiments of the present invention. Embodiments of the present invention permit the accurate and efficient verification of electron treatment fields, as well as photon and mixed beam fields. The result is a radiation therapy device that allows accurate and verifiable delivery of a wide variety of radiation treatments. In some embodiments, detector control 49 may also be used to control the positioning of detector 34. In other embodiments, detector 34 may be positioned manually. In one embodiment, computer 40 operates detector control 49 prior to delivery of a planned treatment protocol to allow the verification of a treatment field.

According to one embodiment of the present invention, computer 40 and detector control 49 perform processing to enhance or manipulate the image captured by detector 34. In one embodiment where detector 34 is used to capture an image of an electron treatment field, computer 40 and detector control 49 perform processing to enhance the image of the bremsstrahlung photons. In particular, processing may be performed to correct for the angular dependence of the bremsstrahlung distribution. Such processing is performed because the bremsstrahlung photons are emitted with an angular distribution about the original electron trajectory. This angular distribution varies with energy of the electrons. In one embodiment, the angular distribution is calculated and corrected using so-called "Schiff distribution" calculations, described in L. Schiff, "Energy-Angle Distribution of Thin Target Bremsstrahlung", Physical Review, 83 (1951), pp. 252–3, the contents of which are incorporated herein by reference for all purposes. In one embodiment, the Schiff distribution is approximated, by calculating the "birth angle" (the relative angle between the bremsstrahlung photon and the initial electron trajectory) as equal to the rest mass of the electron ($m_0c^2$) divided by the rest mass of the electron plus the kinetic energy of the electron prior to the event ($m_0c^2+T_0$). Other approximations may also be used to calculate the angular dependence of the bremsstrahlung photons to the electrons, allowing processing by computer 40 and detector control 49 to correct for the effect.

As a result, processing performed by computer 40 and detector control 49 may be used to correct for this effect and to generate a portal image depicting the patient anatomy and the electron collimator field edge. Applicants have discovered that systems using techniques of the present invention are able to capture images during electron therapy which have resolutions similar to those of conventional portal images of primary photons.

Computer 40 and detector control 49 may also be used to capture multiple electron fields, each of which may be added to each other to depict a relative display of intensity. In such an application, each of the images are compiled separately. Embodiments of the present invention may also be used to capture photon treatment images immediately subsequent to the capture of electron treatment images, thereby allowing the verification of mixed beam treatments. Further details of verification steps will be provided below in conjunction with a description of FIG. 5.

According to another embodiment of the present invention, computer 40 and detector control 49 may be used to take multiple images to generate a representation of the electron treatment field. In one embodiment, computer 40 and detector control 49 may generate an open field image (e.g., an image taken before the patient is positioned on table 16). The image captured by detector 34 will provide a representation of the field defined by electron collimator 62. Computer 40 and detector control 49 are again operated after the patient is positioned on table 16 to take a second portal image. In this second image, a field defined by collimator 62 and showing patient anatomy details will be depicted based on the passage of bremsstrahlung photons through the body. The overall image may be manipulated or processed by combining aspects of the first image with the second image to generate an enhanced image (e.g., as depicted in example screen shots in FIG. 6 which will be described further below).

Computer 40 is also operatively coupled to a dose control unit 50 which includes a dosimetry controller and which is designed to control a beam source 52 to generate a desired beam achieving desired isodose curves. Beam source 52 may be one or more of, for example, an electron, and/or photon beam source. Beam source 52 may be used to generate radiation beams in any of a number of ways well-known to those skilled in the art. For example, beam source 52 may include a dose control unit 50 used to control a trigger system generating injector trigger signals fed to an electron gun in a linear accelerator (not shown) to produce en electron beam as output. Beam source 52 is typically used to generate a beam of therapeutic radiation directed along an axis (as shown in FIG. 1 as item 12) toward treatment zone 18 on patient 22.

According to one embodiment of the invention, the beam generated by beam source 52 is shaped using one or more collimator assemblies, depending on the type of beam generated. For example, in one embodiment, a photon beam produced by beam source 52 is shaped by manipulating a photon collimator 64, while an electron beam produced by beam source 52 is shaped by manipulating an electron collimator 62. According to one embodiment, photon collimator 64 and electron collimator 62 are multi-leaf collimators having a plurality of individually-movable radiation blocking leaves. The leaves of each such collimator are individually driven by a drive unit 58, 59 and are positioned under the control of electron collimator control 54, photon collimator control 55 and sensor(s) 56 and 57.

Drive units 58, 59 move the leaves of each collimator in and out of the treatment field to create a desired field shape for each type of beam. In one embodiment, where an electron beam is to be generated and primary electrons are to be used in a treatment, photon collimator control 55 operates to retract individual leaves of photon collimator 64, while electron collimator control 54 operates to position individual leaves of electron collimator 62 across the path of the electron beam to generate a desired electron field shape at the isocenter. Similarly, in one embodiment, where a photon beam is to be generated and primary photons are to be used in a treatment, electron collimator control 54 operates to retract individual leaves of electron collimator 62 while photon collimator control 55 operates to position individual leaves of photon collimator 64 across the path of the photon beam to generate a desired photon beam field shape at the isocenter. In other embodiments, both collimators 62, 64 may be controlled in concert during the course of a treatment to generate a desired field shape at the isocenter.

Figure 3:
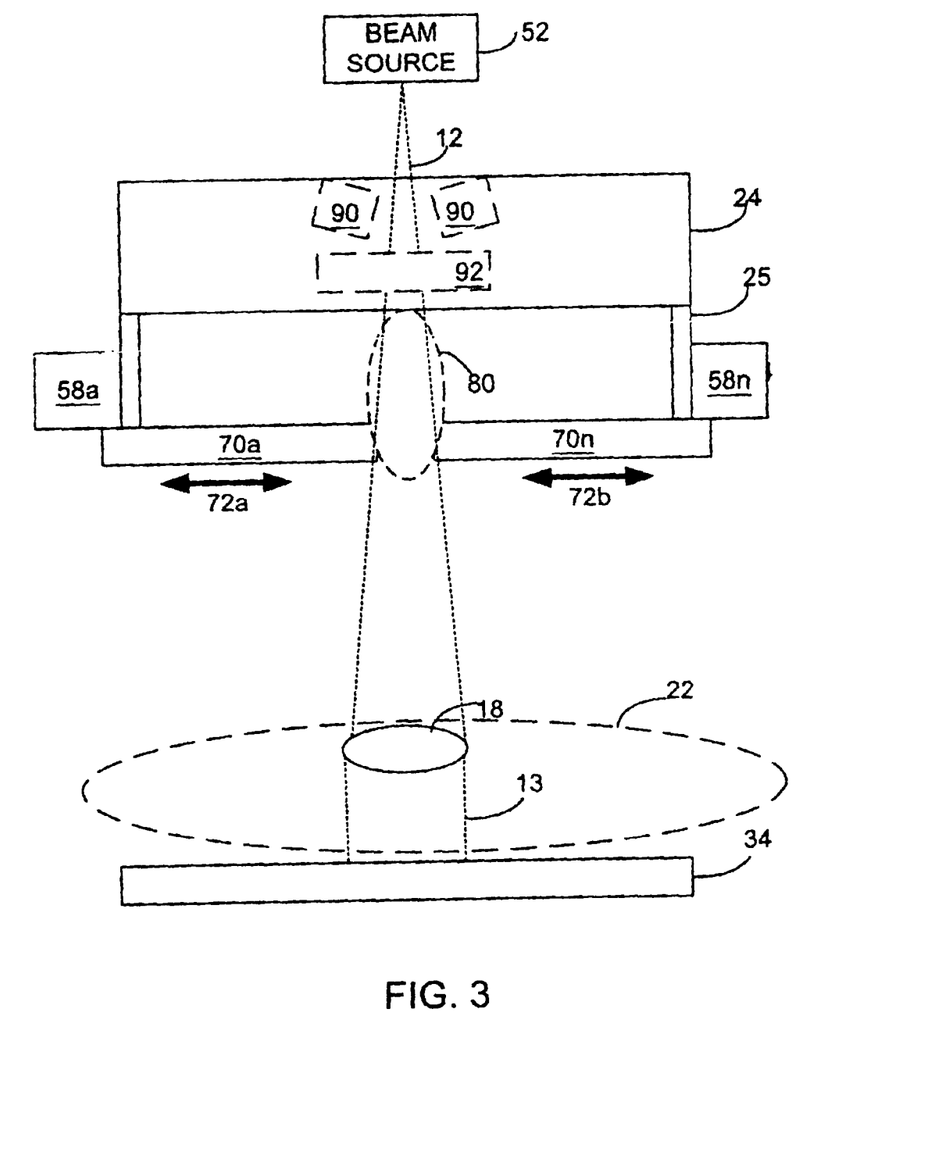
FIG. 3 is a diagram illustrating portions of the radiation therapy device of FIG. 1 according to one embodiment of the present invention.

Referring now to FIG. 3, a perspective view of portions of radiation therapy device 10 is shown. In particular, FIG. 3 depicts portions of treatment head 24 as well as elements along a beam path 12. According to one embodiment of the present invention, treatment head 24 includes an accessory tray 25 or other mounting device positioned between treatment head 24 and treatment area 18. Components of a photon collimator (item 64 of FIG. 2) are shown as collimator blocks 90, 92 in FIG. 3. Collimator blocks 90, 92 are positioned within treatment head 24 and may include a number of individual elements or "leaves" which may be independently controlled to create a desired field shape at the isocenter. Any of a number of known collimators and shaping devices may be used as photon collimator (item 64 of FIG. 2) in conjunction with embodiments of the present invention.

According to one embodiment of the present invention, a separate electron collimator 62 is provided. According to one embodiment of the present invention, components of electron collimator 62 are removably mounted on accessory tray 25, allowing electron collimator 62 to be quickly installed and removed by radiation therapists or other technicians in order to add or remove electron field shaping capabilities to a radiation therapy device. According to one embodiment, individual leaf beds consisting of a number of individual collimator leaves 70a–n are mounted on accessory tray 25 such that they can be moved in a direction 72 across beam path 12. In one embodiment, the individual leaves 70a–n are formed of radiation attenuating materials. For example, brass or tungsten are currently preferred materials, although other materials with similar radiation attenuating characteristics may be used. In one embodiment, individual leaves 70a–n have a width of approximately 1–2 cm. Those skilled in the art will recognize that other shapes and sizes of individual leaves 70a–n may be selected to produce different field shapes at treatment zone 18.

Collimator drives 58a–n and other control circuitry are also removably mounted on accessory tray 25. In one embodiment, collimator drives 58a–n and other control circuitry are mounted on an exterior surface of accessory tray, away from beam path 12, providing greater durability and length of service for the electrical components used to operate electron collimator 62.

According to one embodiment of the present invention, a container 80 (such as a balloon or the like) filled with helium is positioned along a portion of beam path 12 to reduce the amount of free air along beam path 12. In one embodiment, container 80 is removably mounted to accessory tray 25. By replacing some of the air in the air column with helium (or another gas having a low density), the penumbra of the electron beam is reduced, allowing greater control over the shape and effect of the beam at the isocenter. In particular, use of helium along beam path 12 maintains the electron beam spread at a clinically acceptable level by decreasing the number of scattering interactions the electrons experience before they reach treatment zone 18. In operation, a shaped electron field may be delivered to treatment zone 18 by retracting leaves of photon collimator blocks 90, 92, passing the electron beam through helium-filled container 80, and selectively shaping the beam by manipulating electron collimator 62. Multiple fields can thus be delivered to treatment zone 18 during the course of a treatment without manual intervention. Further, embodiments of the present invention support mixed beam treatments by selectively switching between electron and photon beams. According to embodiments of the present invention, manual intervention and equipment set-up is reduced or eliminated.

Applicants have found that mounting components of electron collimator 62 on accessory tray 25 provides several desirable benefits. For example, during most types of treatments, electron collimator 62 provides sufficient patient clearance in all gantry and table positions. Further, electronic components, such as collimator drives 58a–n, will enjoy greater longevity because they are positioned away from beam path 12. Additionally, greater accuracy is provided during treatment because the overall swing weight of treatment head 24 and accessory tray 25 are minimized. The inventive configuration also enjoys the advantage of allowing ready removal and replacement of components. Accessory tray 25, in some embodiments, includes one or more accessory slots (not shown) into which components of electron collimator 62 may fit. In some embodiments, components of electron collimator 62 are installed by simply inserting the components into one or more accessory slots of accessory tray 25. As a result, for treatments that require greater clearance (e.g., such as photon treatments of breast cancer, etc.), components of electron collimator 62 may be readily removed, and then re-installed as needed.

Placement of components of electron collimator 62 on accessory tray 25 also serves to reduce the electron penumbra at the isocenter, providing greater accuracy in the delivery of electron treatments. Those skilled in the art will recognize that the electron penumbra can be reduced further by positioning components of electron collimator 62 closer to the isocenter; however, this increases problems with collision. In some embodiments, additional collision detection and avoidance components may be utilized in radiation therapy device 10 to reduce collisions and to allow closer positioning of components of electron collimator 62.

Beam source 52 directs a beam of therapeutic radiation through treatment head and past collimators 62, 64 towards treatment zone 18 on patient 22. According to one embodiment of the present invention, detector 34 may be positioned downstream of patient 22 to perform field verification pursuant to embodiments of the present invention. As described above, embodiments of the present invention permit field verification for both photon and electron beams. When the beam generated by beam source 52 is an electron beam, bremsstrahlung photons are created in treatment head 24. These photons (represented in FIG. 3 as item 13) pass through patient 22 and are detected by detector 34.

Figure 4:
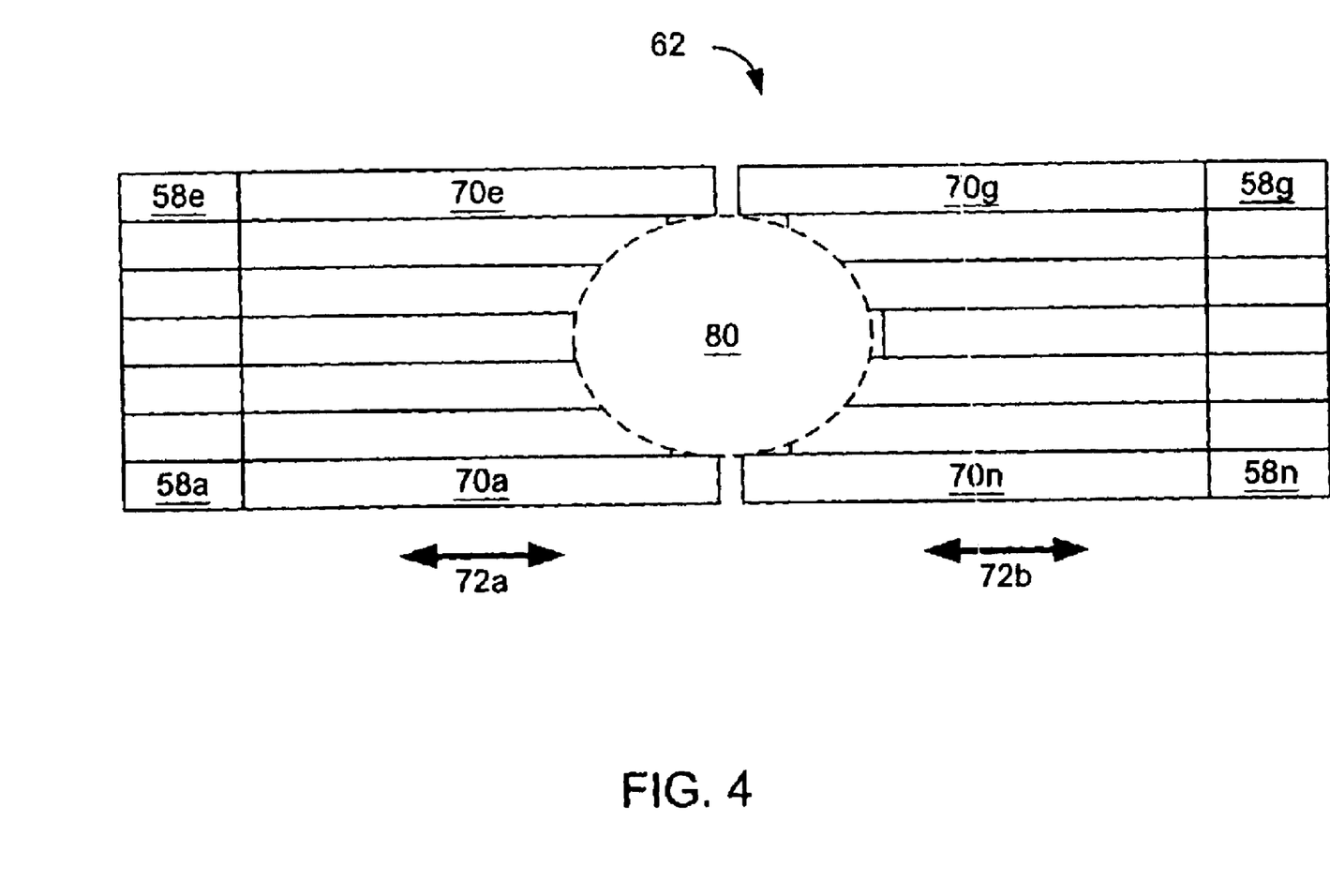
FIG. 4 is a diagram illustrating a collimator for use in a radiation therapy device according to one embodiment of the present invention.

Referring now to FIG. 4, details regarding the construction of electron collimator 62 are shown. FIG. 4 is a beams eye view of electron collimator 62, showing the placement of container 80 in relation to components of electron collimator 62. In one embodiment, electron collimator 62 includes a plurality of individual collimator drives 58a–n each coupled to drive individual leaves 70a–n of the collimator. As depicted, individual leaves 70a–n may be positioned using collimator drives 58a–n to generate a desired collimator shape, thereby producing a desired electron field shape at the treatment area on a patient.

Figure 5A:
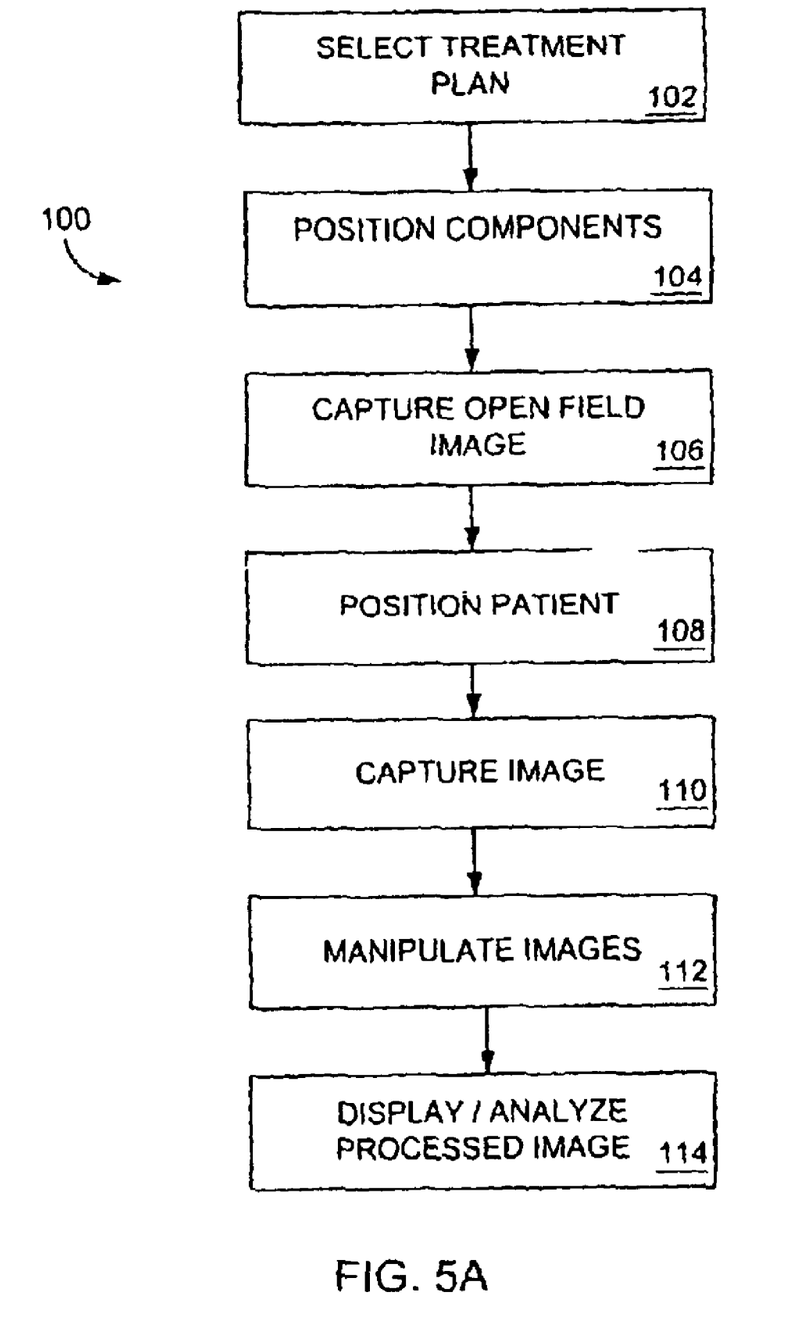
FIGS. 5A and 5B are a diagrams illustrating processes for treatment field verification according to embodiments of the present invention.
Figure 5B:
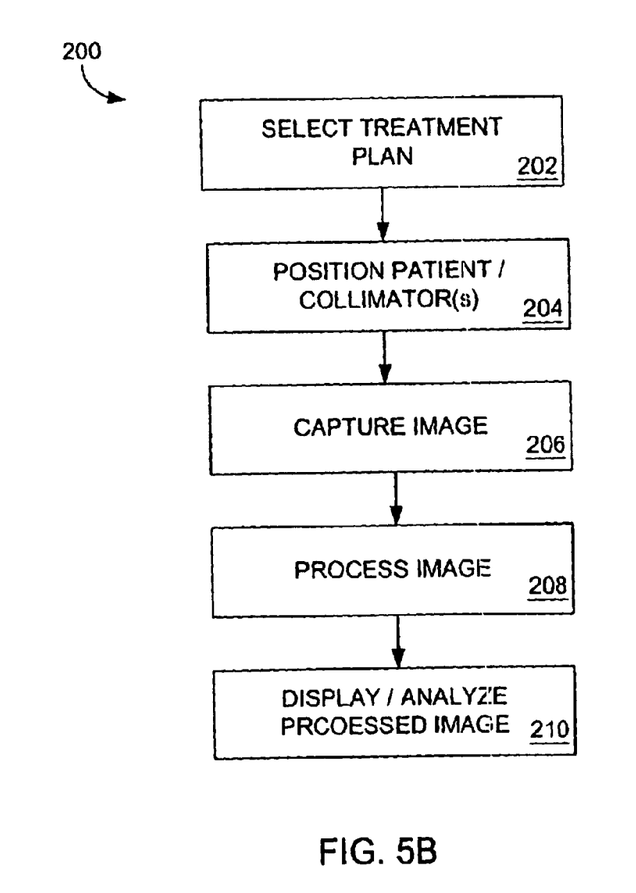

Referring now to FIG. 5A, a flow diagram is shown depicting one embodiment of a process 100 for image verification using embodiments of the present invention. This processing may be performed under the control of computer program code stored at, or accessible by, computer 40 of treatment processing unit 32. The particular arrangement of elements in the flow charts of FIG. 5A (or 5B) are not meant to imply a fixed order to the steps; embodiments of the present invention can be practiced in any order that is practicable.

Process 100 may be performed at any stage during radiation therapy or radiation therapy pre-planning. In one embodiment, process 100 is performed just prior to delivery of a prescribed radiation therapy to determine if the patient is properly positioned and to determine if the field shape conforms to the planned treatment. In one embodiment, process 100 is performed when a mixed mode or primary electron therapy is to be delivered. Processing begins at 102 where a treatment plan is selected. This treatment plan may be based on data stored at, or accessible to, computer 40 of treatment processing unit 32. The treatment plan will define the type of radiation to be delivered (e.g., electron, photon, or mixed-beam), as well as the positioning of the patient and the electron and/or photon collimators.

Processing continues at 104 where computer 40 directs various control units to position components such as the table, the gantry, the detector, and the electron and photon collimators in the positions defined by the treatment plan selected at 102. For example, in an embodiment where electron radiation will be used to treat a patient, computer 40 may direct photon collimator control 55 to retract the photon collimator leaves away from the beam path and the electron collimator control 54 to position the electron collimator leaves to create a desired field shape.

Processing continues at 106 where an open field image is captured on detector 34 (e.g., an image taken before the patient is positioned on table 16). Processing at 106 includes the generation of a radiation beam of a desired intensity and type directed toward the treatment zone, and capturing an image of the treatment field delivered to detector 34. This open field image captured at 106 is stored, at least temporarily, for later access and manipulation by computer 40. The image captured at 106 is performed by enabling detector 34. In some embodiments, detector 34 is first reset before capturing the image to ensure that elements of the detector are ready to capture an image. As described above, various steps of process 100 may occur in a different sequence than described herein. As one example, the open field image captured at 106 may be captured at other times during (or before, or after) process 100 (e.g., the open field image may be captured after the image captured with the patient in position, or after step 110, discussed below).

Processing continues at 108 where the patient to be treated is positioned on table 16. Processing continues at 110 where a further image is captured on detector 34. Processing at 110 includes the generation of a radiation beam of a desired intensity and type directed toward the treatment zone, and capturing an image of the treatment field delivered to detector 34. According to one embodiment of the present invention, processing at 110 includes the capture of bremsstrahlung photons which pass through the patient. As described above, bremsstrahlung photons are generated in treatment head 24 and further by scattering caused by collimators and other high atomic number materials along the beam path. The image captured at 110 is performed by enabling detector 34. In some embodiments, detector 34 is first reset before capturing the image to ensure that elements of the detector are ready to capture an image.

Figure 6:
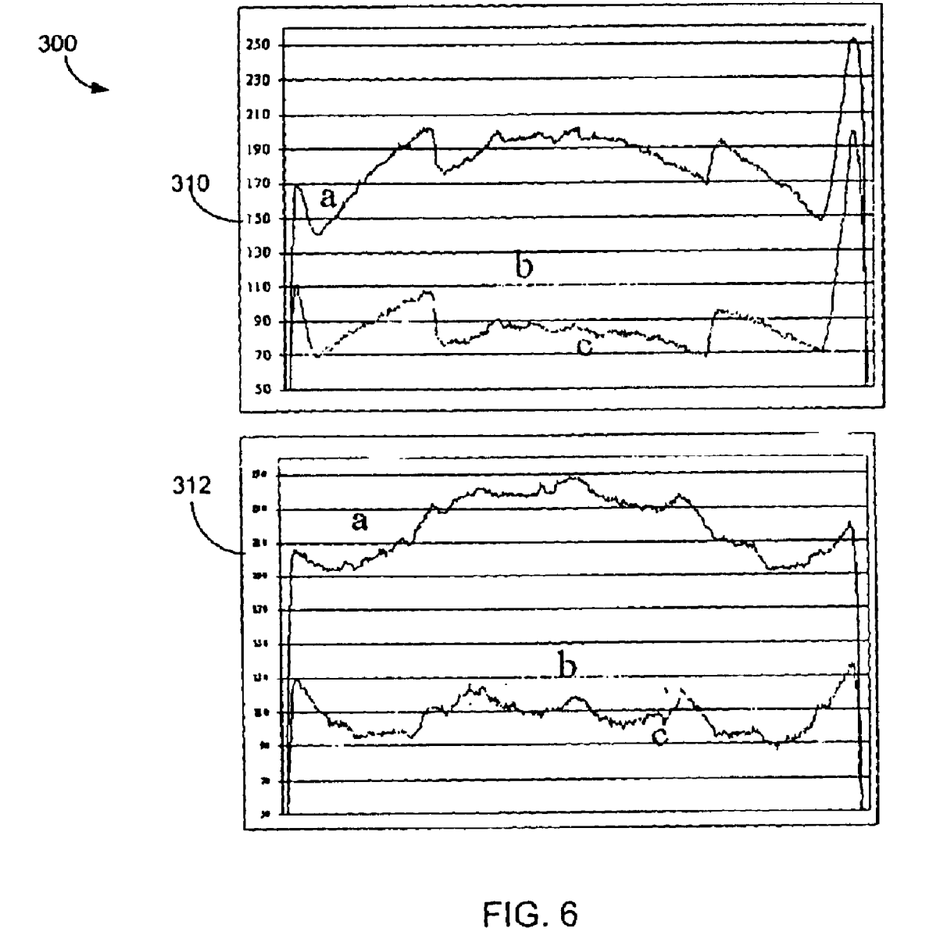
FIG. 6 are representative images captured using an embodiment of the present invention.

Once the image has been captured at 110, processing continues at 112 where both the open field image (captured at 106) and the further image (captured at 110) are manipulated or enhanced. Example images captured are shown at FIG. 6, where each of the example screens 310, 312 depict a plot of grayscale vs. detector element position for one row of detector elements of detector 34. Each example screen 310, 312 depicts a first curve (curve a) showing a base image captured with a patient (or a phantom) in place. The outermost bumps on both sides correspond to the edges of the images, and the innermost bumps represent the field edges. Each example screen 310, 312 also depicts a second curve (curve b) showing an open field image captured without a patient (or phantom) in position. When corresponding detector element values for each detector element are subtracted from those with the patient in place, a corrected image (curve c) is produced. Such processing ensures that individual differences in elements of detector 34 are corrected as well.

Processing continues at 114 where the processed image is displayed and/or analyzed. In some embodiments, the image is displayed on operator display console 42 for viewing and analysis by a radiation therapist. In some embodiments, the image is automatically analyzed by comparing the detected image with an expected image. Those skilled in the art will recognize that a number of portal imaging and image processing techniques may be utilized to manipulate and analyze images captured using techniques of the present invention. Analysis at 114 may indicate that the treatment field is not properly shaped, and/or that the patient is not properly positioned. Corrective action may be taken to reposition the patient. In some situations, corrective action may also include repositioning components of radiation therapy device 10 such as one or more collimators, the gantry, the table, etc. In some embodiments, process 100 may be repeated to further verify the treatment field. Once the detected treatment field is satisfactory, the prescribed course of treatment may be administered.

Referring now to FIG. 5B, a further embodiment of the present invention is shown depicting a process 200 for verifying an electron treatment field generated by radiation therapy device 10 of FIG. 1. Process 200 may be performed at any stage during radiation therapy or radiation therapy pre-planning. In one embodiment, process 200 is performed just prior to delivery of a prescribed radiation therapy to determine if the patient is properly positioned and to determine if the field shape conforms to the planned treatment. Processing begins at 202 where a treatment plan is selected. This treatment plan may be based on data stored at, or accessible to, computer 40 of treatment processing unit 32. The treatment plan will define the type of radiation to be delivered (e.g., electron, photon, or mixed-beam), as well as the positioning of the patient and the electron and/or photon collimators.

Processing continues at 204 where computer 40 directs various control units to position the table, the gantry, the detector, and the electron and photon collimators in the positions defined by the treatment plan selected at 202. For example, in an embodiment where electron radiation will be used to treat a patient, computer 40 may direct photon collimator control 55 to retract the photon collimator leaves away from the beam path and the electron collimator control 54 to position the electron collimator leaves to create a desired field shape.

Processing continues at 206 where an image is captured on detector 34. Processing at 106 includes the generation of a radiation beam of a desired intensity and type directed toward the treatment zone. If a portal image is to be captured of an electron treatment, an electron beam is generated by radiation therapy device 10. Bremsstrahlung photons, as described above, are generated in treatment head 24 and further by scattering caused by collimators and other high atomic number materials along the beam path. These bremsstrahlung photons pass through the patient and are detected by detector 34 that is positioned along the beam path, downstream from the treatment zone. If a portal image is to be captured of a photon treatment, a photon beam is generated by radiation therapy device 10. The photons pass through the patient and are detected by detector 34. The image captured at 206 is performed by enabling detector 34. In some embodiments, detector 34 is first reset before capturing the image to ensure that elements of the detector are ready to capture an image.

Once an image has been captured at 206, processing continues at 208 where the image is manipulated or enhanced. The nature of the processing conducted at 206, in some embodiments, will depend on the type of radiation treatment to be verified. For example, processing at 208 will be different for an electron treatment verification than for photon treatment verification. In particular, processing at 208 for electron treatment verification, in one embodiment, involves processing to correct the angular dependence of the bremsstrahlung photons that are detected at 206 (e.g., by applying the Schiff distribution or similar formula). Processing at 208 may include first calculating a known bremsstrahlung photon angle, assuming that most of these photons are created from a virtual source in the head at the incident electron energy. This angle is projected to the plane of detector 34 and the cosine times the distance from the virtual source to the plane of the detector 34 is found. The number of detector elements in detector 34 that could be encompassed by this distance (n) is noted. For each detector element, the signal is divided by the number of detector elements that fall within the distance (n) from the detector element. The signal at the detector element is then evenly divided to be applied between the detector elements within its reach. This information may be stored in a two dimensional correction matrix (e.g., at or accessible to computer 40). This processing may be repeated for each detector element in detector 34. The correction matrix is then applied to enhance the image captured at 206.

Processing at 208 to manipulate a photon treatment image may involve standard image processing techniques to produce a clear image. In some embodiments, no processing may be required to manipulate or enhance a photon treatment image.

Processing continues at 210 where the image captured at 206 and enhanced at 208 is displayed and/or analyzed. In some embodiments, the image is displayed on operator display console 42 for viewing and analysis by a radiation therapist. In some embodiments, the image is automatically analyzed by comparing the detected image with an expected image. Those skilled in the art will recognize that a number of portal imaging and image processing techniques may be utilized to manipulate and analyze images captured using techniques of the present invention. Analysis at 210 may indicate that the treatment field is not properly shaped, and/or that the patient is not properly positioned. Corrective action may be taken to reposition the patient. In some situations, corrective action may also include repositioning components of radiation therapy device 10 such as one or more collimators, the gantry, the table, etc. In some embodiments, process 200 may be repeated to further verify the treatment field. Once the detected treatment field is satisfactory, the prescribed course of treatment may be administered.

Those skilled in the art will appreciate that various adaptations and modifications of the just described preferred embodiments can be configured without departing from the scope and spirit of the invention. For example, although the use of imaging devices such as flat panel detectors have been described, some imaging of the present invention may also be performed using sufficiently-sensitive film. In some embodiments, some or all of the imaging of the present invention may be captured using imaging detectors based on video capture technologies having sufficient sensitivity to capture the images described herein.

Example testing of radiation therapy devices 10 using embodiments of the present invention have shown desirable results. As an example, electron beam verification using a device configured pursuant to one embodiment of the present invention was demonstrated within the clinical dose delivery time and collimator leaf shapes were verified using a detector positioned 140 cm from the source for a variety of energies from 6 to 21 MeV. In the example embodiment, detector 34 was a large scale array (1024 by 1024) of elements. For each energy, 10 cm of solid water were placed in the treatment field to stop the electrons and a gain correction image was acquired by the detector to compensate for the bremsstrahlung angular dependence. Several integration time factors were tested to obtain verification images within 50 Monitor Units, a typical number for electron treatments. Monte Carlo calculations using EGS4/BEAM were performed to calculate the expected attenuation of photons from a realistic beam passing through high-Z material just thick enough to stop the electron beams (a reasonable thickness for an electron collimator). Profiles extracted from the images acquired with electron beams under similar conditions show agreement with the calculations. Las Vegas and Rando phantom images acquired with electron beams show remarkably high contrast and very good spatial resolution. Embodiments of the present invention were able to acquire images at each of the tested energies with less than 50 Monitor Units. Other embodiments and configurations of the present invention may also be used, as will be described herein, to produce similar results. The above-described test configuration is not intended to be limiting, but rather is presented as an example of one embodiment of the present invention.

Although a preferred embodiment utilizing removable electron collimator components has been described, in one embodiment, the electron collimator components may be mounted in a manner that does not facilitate ready removal. Therefore, it is to be understood that, within the scope of the appended claims, the invention may be practiced other than as specifically described herein.

What is claimed is:

1. A method for verifying an electron treatment field created by an electron treatment beam, comprising:

directing the electron treatment beam from a treatment head toward a location to be irradiated;

positioning an imaging device downstream from the location to be irradiated; and operating said imaging device to detect an image created by photons produced incidental to the delivery of said electron treatment beam to said location.

2. The method of claim 1, further comprising:

enhancing said image to generate a representation of said electron treatment field.

3. The method of claim 2, wherein said enhancing further comprises:

determining an energy of said electron treatment beam;

calculating an angular dependence of said photons on said electron treatment beam; and generating said representation of said electron treatment field based on said detected image and said angular dependence.

4. The method of claim 2, wherein said enhancing further comprises:

comparing said image to an open field image to generate an enhanced image of said electron treatment field.

5. The method of claim 2, further comprising:

displaying said representation of said electron treatment field on an operator display console.

6. The method of claim 2, further comprising:

comparing said representation of said electron treatment field to a desired image of said electron treatment field.

7. The method of claim 6, further comprising:
adjusting at least one of a collimator position and a patient position if said comparison indicates that said representation of said electron treatment field is different from said desired image of said electron treatment field.

8. The method of claim 1, wherein said imaging device is a flat panel imaging device.

9. The method of claim 8, wherein said flat panel imaging device comprises a plurality of solid state sensors.

10. The method of claim 9, wherein said solid state sensors are amorphous silicon sensors.

11. The method of claim 1, wherein said imaging device comprises video technology.

12. A method for verifying a treatment field in a radiation therapy device, comprising:
directing an electron beam at an object to be irradiated;
collimating said electron beam to generate an electron treatment field; and
detecting, using an imaging device, an image created by a plurality of photons after passing through said object, said plurality of photons contained within said electron treatment field and produced incidental to said electron beam.

13. The method of claim 12, further comprising:
enhancing said image to generate a representation of said electron treatment field.

14. The method of claim 13, further comprising:
comparing said representation with a desired image of said electron treatment field; and
repositioning at least one of said body and a collimator device if said comparing indicates that said representation is not within an expected tolerance of said desired image.

15. The method of claim 13, wherein said enhancing further comprises:
determining an energy of said electron treatment beam;
calculating an angular dependence of said photons on said electron treatment beam; and
generating said representation of said electron treatment field based on said detected image and said angular dependence.

16. The method of claim 12, wherein said plurality of photons are bremsstrahlung photons.

17. The method of claim 12, further comprising:
positioning an imaging device beneath a treatment zone;
directing an electron beam at said treatment zone;
collimating said electron beam to generate an electron treatment field;
detecting, using said imaging device, an open field image; and
comparing said open field image with said image to produce a representation of said electron treatment field.

18. A radiation treatment field verification method, comprising:
generating a radiation treatment beam comprised of one of primary electrons and primary photons;
selectively shaping said radiation treatment beam to create a radiation treatment field on an object;
detecting components of said radiation treatment beam on an imaging device positioned downstream of said object; and
generating a representation of said radiation treatment field.

19. The method of claim 18, wherein said radiation treatment beam comprises primary electrons and wherein said components of said radiation treatment beam are bremsstrahlung photons generated within said radiation treatment beam.

20. The method of claim 19, wherein said generating a representation further comprises:
determining an energy of said primary electrons;
calculating an angular dependence of said bremsstrahlung photons on said primary electrons; and
generating said representation of said radiation treatment field based on said detected components and said angular dependence.

21. The method of claim 19, wherein said generating a representation further comprises:
generating an open field representation of said radiation treatment field; and
comparing said open field representation with said components detected downstream of said body to generate said representation of said radiation treatment field.

22. The method of claim 18, wherein said radiation treatment beam comprises primary photons and wherein said components of said radiation treatment beam are photons of said radiation treatment beam.

23. The method of claim 18, wherein said selectively shaping is performed by controllably positioning a photon collimator and an electron collimator.

24. A radiation therapy device, comprising:
an image detector positioned downstream from a body being irradiated by an electron beam and capturing a radiation image, said electron beam having a field shape at said object; and
a computing device coupled to said image detector and operative to enhance said radiation image to generate a representation of said radiation image.

25. The radiation therapy device of claim 24, further comprising:
a display device coupled to said computing device and displaying said representation of said radiation image.

26. The radiation therapy device of claim 24, further comprising:
at least a first collimating device positioned along a path of said electron beam and controllably positioned to generate said field shape.

27. A system for verifying an electron treatment field, comprising:
means for directing an electron treatment beam from a treatment head toward a location to be irradiated;
means for positioning an imaging device downstream from the location to be irradiated; and
means for operating said imaging device to detect an image create by photons produced incidental to the delivery of said electron treatment field to said location.

* * * * *